US010676564B2

(12) United States Patent
Vedage et al.

(10) Patent No.: US 10,676,564 B2
(45) Date of Patent: Jun. 9, 2020

(54) AMIDOAMINE AND POLYAMIDE CURING AGENTS, COMPOSITIONS, AND METHODS

(71) Applicant: Evonik Operations GmbH, Essen (DE)

(72) Inventors: Gamini Ananda Vedage, Bethlehem, PA (US); Shiying Zheng, Center Valley, PA (US); Kathryn Sue Hayes, Plymouth Meeting, PA (US)

(73) Assignee: Evonik Operations GmbH, Essen (DE)

( * ) Notice: Subject to any disclaimer, the term of this patent is extended or adjusted under 35 U.S.C. 154(b) by 43 days.

(21) Appl. No.: 15/394,991

(22) Filed: Dec. 30, 2016

(65) Prior Publication Data

US 2017/0218115 A1    Aug. 3, 2017

Related U.S. Application Data

(60) Provisional application No. 62/290,015, filed on Feb. 2, 2016.

(51) Int. Cl.

| | |
|---|---|
| *C08G 59/54* | (2006.01) |
| *C08G 59/44* | (2006.01) |
| *C08G 59/24* | (2006.01) |
| *C07C 233/38* | (2006.01) |
| *C07C 209/48* | (2006.01) |
| *C08G 59/48* | (2006.01) |
| *C07C 231/02* | (2006.01) |

(52) U.S. Cl.
CPC ............ *C08G 59/54* (2013.01); *C07C 209/48* (2013.01); *C07C 231/02* (2013.01); *C07C 233/38* (2013.01); *C08G 59/245* (2013.01); *C08G 59/44* (2013.01); *C08G 59/48* (2013.01)

(58) Field of Classification Search
CPC ................................ C08G 59/54; C08G 59/40
See application file for complete search history.

(56) References Cited

U.S. PATENT DOCUMENTS

| | | | |
|---|---|---|---|
| 2,705,223 A | 3/1955 | Renfrew et al. | |
| 4,463,157 A | 7/1984 | Kersten et al. | |
| 8,293,863 B2 | 10/2012 | Vedage et al. | |
| 2007/0287808 A1 | 12/2007 | Vedage et al. | |
| 2007/0287809 A1* | 12/2007 | Vedage | C08G 59/44 525/423 |
| 2008/0227928 A1 | 9/2008 | Vedage et al. | |
| 2012/0190799 A1 | 7/2012 | Anbazhagan et al. | |
| 2012/0237774 A1 | 9/2012 | Raymond et al. | |

FOREIGN PATENT DOCUMENTS

| | | |
|---|---|---|
| EP | 1865013 A1 | 12/2007 |
| GB | 2031431 A | 4/1980 |
| WO | 2005123802 A1 | 12/2005 |

OTHER PUBLICATIONS

PCT International Search Report dated May 15, 2017 corresponding to PCT International Application No. PCT/US2017/015802 filed Jan. 31, 2017 (6 pages).

* cited by examiner

*Primary Examiner* — Kuo Liang Peng
(74) *Attorney, Agent, or Firm* — Andrew H. Chung; Linda S. Li; Jason S. Ngui

(57) ABSTRACT

A composition including an amidoamine curing agent composition or a polyamide curing agent composition are disclosed. The composition includes the reaction products of (1) an amine component including at least one multifunctional amine of structure (I):

$$\begin{array}{c} R_1 \\ R\diagdown \quad | \quad \diagdown \\ N-(CH_2)_n-N-(CH_2)_n-N[(CH_2)_3NH]_m-H \\ R\diagup \qquad \qquad \diagup \\ R \end{array} \quad (I)$$

wherein each R is independently H or $CH_2CH_2CH_2NH_2$; $R_1$ is H, $CH_3CH_2CH_2N-$, C1-C21 alkyl, or C1-C21 alkenyl; n is 2; and m is 1 or 2, with (2) a fatty acid or ester component selected from the group consisting of a dimer fatty acid or ester component, a monofunctional fatty acid or ester component, and combinations thereof. The amidoamine curing agent composition remains as liquid at ambient temperature.

16 Claims, No Drawings

AMIDOAMINE AND POLYAMIDE CURING AGENTS, COMPOSITIONS, AND METHODS

BACKGROUND OF THE INVENTION

The present invention is directed to a composition and a method for forming amidoamines and polyamides from polyalkylene polyamines. More specifically, the present invention is directed to amidoamine curing agent compositions formed from polyalkylene polyamines and epoxy-amine compositions.

Polyamide and amidoamine epoxy curing agents are utilized extensively in many markets including protective metal and concrete coatings, adhesives and sealants, composites, and electrical encapsulation. Polyamide epoxy curing agents comprise the reaction products of dimerized fatty acids (dimer fatty acid) or esters and polyethylene polyamines, and usually a certain amount of monomeric fatty acid, which helps to control molecular weight and viscosity. "Dimerized" or "dimer" or "polymerized" fatty acid refers, in a general way, to polymerized fatty acids obtained from unsaturated fatty acids.

Dimer fatty acid is usually prepared by the acid-catalyzed oligomerization of monomeric unsaturated fatty acids under pressure probably by a Diels Alder mechanism. Usually tall oil fatty acid (TOFA) is used, although other plant fatty acids occurring in natural oils, such as soya oil, linseed oil, tung oil, perilla oil, oiticica oil, cornseed oil, sunflower oil, safflower oil, dehydrated castor oil, and the like, can be used as well. Commercial products of dimer fatty acids generally consist of mostly (>70%) dimeric species, with the rest consisting mostly of trimers and higher oligomers, along with small amounts (generally less than 5%) of monomeric fatty acids. Common monofunctional unsaturated C16 to C22 fatty acids also employed with the dimer fatty acids in making polyamides include tall oil fatty acid (TOFA), soya oil, linseed oil, cottonseed oil, or the like.

Amidoamine epoxy curing agents comprise the reaction products of monofunctional higher fatty acids or esters and polyethylene polyamines. The monofunctional higher fatty acids represent both saturated fatty acids, and unsaturated fatty acids with one or more double bonds. Examples of monofunctional unsaturated fatty acids occurring in natural oils, such as linseed oil, tall oil (tall oil fatty acid (TOFA)) and dehydrated castor oil, are a mixture of 9,11-octadecadienic acid (2 double bonds), 9,12-octadecadienic acid (2 double bonds), oleic acid (1 double bond), linoleic acid (2 double bonds), linolenic (3 double bonds), alpha-eleostearic acid (3 double bonds) and beta-eleostearic acid (3 double bonds). Examples of saturated fatty acid occurring in natural oils include lauric acid (C12), myristic (C14), palmitic acid (C16), and steric acid (C18). Appropriate synthetic fatty acids can also serve as starting material for amidoamine curing agents. The fatty acid can be used individually or as a mixture of more than one fatty acid. Commonly used fatty acids for amidoamines include tall oil fatty acid (TOFA), soya oil, linseed oil, cottonseed oil, or the like. Small amounts of dimer acid can also be incorporated into amidoamine synthesis.

The polyethylene polyamines, such as diethylene triamine (DETA), triethylene tetramine (TETA), tetraethylene pentamine (TEPA), pentaethylene hexamine (PEHA), hexaethylene heptamine (HEHA), and the like, are employed in the preparation of polyamide and amidoamine curing agents. In actual commercial practice, the polyethylene polyamine most commonly employed in polyamide preparation is TETA and TEPA in amidoamine synthesis.

In addition, other monofunctional or difunctional carboxylic acids, or other multifunctional polyamines, may be incorporated into the condensation process in order to provide specialized property enhancements for polyamide and amidoamine curing agents.

Polyethylene polyamines are conventionally manufactured from the reaction of ammonia with either ethylene dichloride or ethanolamine. As new manufacturing assets are built to produce polyethylene polyamines, there is a tendency to favor the ethanolamine process, as it is less corrosive to the manufacturing equipment, and hence, more economical. Unfortunately, the ethanolamine process generally produces a lower yield of higher polyethylene polyamines, such as TETA and TEPA, than the ethylene dichloride process, and therefore prices for TETA and TEPA are increasing relative to the prices for other polyethylene polyamines. Furthermore, the demand for higher polyethylene polyamines, especially TEPA, is increasing. There is therefore a need for more economical alternatives to TETA, and especially TEPA, in the manufacture of polyamide and amidoamine curing agents.

Several methods for preparation of polyamide and amidoamine and their use as epoxy curing agents are known. For example, U.S. Pat. No. 2,705,223 describes epoxy resins cured with polyamides based on polymeric fatty acids and polyethyleneamines.

GB 2,031,431 discloses epoxy resins cured with mixtures of high molecular weight polyoxyalkylene polyamines and N,N'-bis(3-aminopropyl)ethylenediamine.

U.S. Pat. No. 4,463,157 discloses self-curing, amide-group-containing aminourea resins produced from a polyaminoamide, which has been produced from polyalkylene-polyamines reacted with fatty acids and/or from polyalkylene-polyamines reacted with dimer fatty acids. Table 1 of U.S. Pat. No. 4,463,157 shows the product of reaction of N,N'-bis(3-aminopropyl)ethylenediamine with ricinene fatty acid.

U.S. Pat. No. 8,293,863 discloses polyamide curing agent compositions, including the reaction products of (1) multifunctional amines of the following structure:

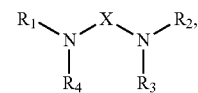

wherein $R_1$ is $CH_2CH_2CH_2NH_2$; $R_2$, $R_3$ and $R_4$ independently are H or $CH_2CH_2CH_2NH_2$, and X is $CH_2CH_2$ or $CH_2CH_2CH_2$, with (2) dimer fatty acids, optionally in combination with monofunctional fatty acids. The reaction product may include at least 15 wt % tetrahydropyrimidine-containing components.

The disclosure of the foregoing publications, including patents and patent applications, is hereby incorporated by reference.

BRIEF SUMMARY OF THE INVENTION

In an exemplary embodiment, a polyamide curing agent composition. The polyamide curing agent composition includes the reaction products of (1) an amine component including at least one multifunctional amine of structure (I):

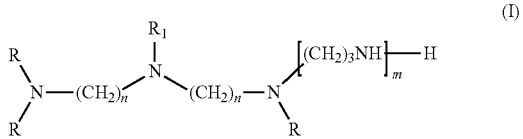

wherein each R is independently H or $CH_2CH_2CH_2NH_2$; $R_1$ is H, $CH_2CH_2CH_2N$, C1-C21 alkyl, or C1-C21 alkenyl; n is 2; and m is 1 or 2, with (2) a dimer fatty acid or ester component, optionally, containing a monofunctional fatty acid or ester. The polyamide curing agent composition remains as liquid at ambient temperature. In another embodiment, the polyamide curing agent composition remains as liquid through a temperature range of about 5 degrees Celsius to about 40 degrees Celsius.

In an exemplary embodiment, an amidoamine curing agent composition. The amidoamine curing agent composition includes the reaction products of (1) an amine component including at least one multifunctional amine of structure (I):

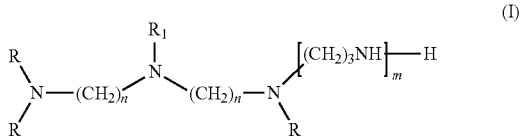

wherein each R is independently H or $CH_2CH_2CH_2NH_2$; $R_1$ is H, $CH_3CH_2CH_2N$—, C1-C21 alkyl, or C1-C21 alkenyl; n is 2; and m is 1 or 2, with (2) a monofunctional fatty acid or ester component, optionally, containing a dimer fatty acid or ester. The amidoamine curing agent composition remains as liquid at ambient temperature. In another embodiment, the amidoamine curing agent composition remains as liquid through a temperature range of about 5 degrees Celsius to about 40 degrees Celsius.

In one exemplary embodiment, $R_1$ is H.

In another exemplary embodiment, the amine component (1) that is reacted with the dimer fatty acid or ester component, or monofunctional fatty acid or ester component, or both dimer acid or ester and monofunctional fatty acid or ester components includes a mixture of amines of structure (I) in a suitable parts-by-weight (pbw) ratio of 0 to 50 pbw amine having 4 nitrogen atoms (N4), 40 to 95 pbw amine having 5 nitrogen atoms (N5), and 0 to 50 pbw amine having at least 6 nitrogen atoms (N6 and higher amine); or a more suitable ratio of 0 to 30 pbw amine having 4 nitrogen atoms (N4), 40 to 95 pbw amine having 5 nitrogen atoms (N5), and 0 to 50 pbw amine having at least 6 nitrogen atoms (N6 and higher amine); or a suitable ratio of 0 to 20 pbw amine having 4 nitrogen atoms (N4), 50 to 95 pbw amine having 5 nitrogen atoms (N5), and 0 to 40 pbw amine having at least 6 nitrogen atoms (N6 and higher amine); or a suitable ratio of 0 to 20 pbw amine having 4 nitrogen atoms (N4), 50 to 90 pbw amine having 5 nitrogen atoms (N5), and 3 to 35 pbw amine having at least 6 nitrogen atoms (N6 and higher amine); or a suitable ratio of 1 to 15 pbw amine having 4 nitrogen atoms (N4), 50 to 90 pbw amine having 5 nitrogen atoms (N5), and 5 to 35 pbw amine having at least 6 nitrogen atoms (N6 and higher amine); or a suitable ratio of 0 to 25 pbw amine having 4 nitrogen atoms (N4), 40 to 95 pbw amine having 5 nitrogen atoms (N5), and 0 to 45 pbw amine having at least 6 nitrogen atoms (N6 and higher amine); or a suitable ratio of 1 to 20 pbw amine having 4 nitrogen atoms (N4), 40 to 90 pbw amine having 5 nitrogen atoms (N5), and 0 to 35 pbw amine having at least 6 nitrogen atoms (N6 and higher amine).

In another exemplary embodiment, the polyamide curing agent composition, i.e., the reaction product of the amine component and the dimer fatty acid component, includes at least 15 mol % tetrahydropyrimidine-containing components.

In yet another exemplary embodiment, the amidoamine curing agent composition, i.e., the reaction product of the amine component and the monofunctional fatty acid component, includes at least 3 mol % tetrahydropyrimidine-containing components.

In another exemplary embodiment, there are provided epoxy systems or compositions, including the contact product of the above polyamide and amidoamine curing agent, or curative, and an epoxy resin.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

Provided are amine-epoxy curing agents, amine-epoxy curing compositions and methods for forming cured epoxy. Amine-epoxy curing agents, according to the present invention, often provide similar or faster cure speed than conventional polyamide and amidoamine curing agents. As another advantage of the present invention, curing agent compositions are provided which do not contain triethylenetetramine (TETA) or tetraethylenepentamine (TEPA), but which have physical properties including viscosity, molecular weight and amine hydrogen equivalent weight (HEW) that closely resemble conventional polyamides and amidoamines derived from triethylenetetramine (TETA) or tetraethylenepentamine (TEPA). Suitable applications include, but are not limited to, coatings, adhesives, floorings, composites, and other articles. Thus, another embodiment of the invention includes coatings, adhesives, floorings, composites, and other cured epoxy articles prepared by curing epoxy resins using such curing agents.

As another advantage, when the polyamide curing agent composition contains at least 15 mol % tetrahydropyrimidine-containing components, the curing agent composition affords 2-component polyamide coatings manifesting good coating appearance and faster dry speeds compared to conventional polyamide from TEPA/TOFA.

As yet another advantage, the amidoamine curing agent composition and the polyamide curing agent composition remain as liquid at wide temperature range of 5 degrees Celsius to 40 degrees Celsius, and affords 2-component epoxy-amidoamine coatings and epoxy-polyamide coatings with good coating appearance and fast dry speeds. In particular, the curing agent composition remains liquid at ambient temperatures. As utilized herein, ambient temperature is room temperature or about 25 degrees Celsius.

Polyamide curing agent compositions include the reaction products of (1) an amine component including at least one multifunctional amine of structure (I):

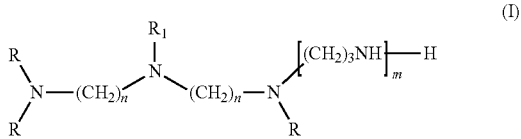

wherein each R is independently H or $CH_2CH_2CH_2NH_2$; $R_1$ is H, $CH_3CH_2CH_2N—$, C1-C21 alkyl, or C1-C21 alkenyl; n is 2; and m is 1 or 2, with (2) a dimer fatty acid or ester component, optionally, containing a monofunctional fatty acid or ester.

Amidoamine curing agent compositions include the reaction products of (1) an amine component including at least one multifunctional amine of structure (I):

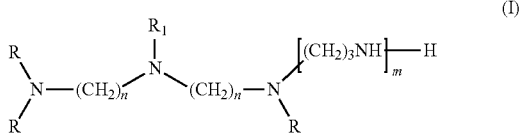

wherein each R is independently H or $CH_2CH_2CH_2NH_2$; $R_1$ is H, $CH_3CH_2CH_2N—$, C1-C21 alkyl, or C1-C21 alkenyl; n is 2; and m is 1 or 2, with (2) a monofunctional fatty acid or ester component, optionally, containing a dimer fatty acid or ester. In one exemplary embodiment, the amine component that is reacted with the dimer fatty acid or ester or monofunctional fatty acid component includes a mixture of amines of structure (I) in a parts-by-weight (pbw) ratio of 0 to 50 pbw amine having 4 nitrogen atoms (N4), 40 to 95 pbw amine having 5 nitrogen atoms (N5), and 0 to 50 pbw amine having at least 6 nitrogen atoms (N6 and higher amine); or a more suitable ratio of 0 to 30 pbw amine having 4 nitrogen atoms (N4), 40 to 95 pbw amine having 5 nitrogen atoms (N5), and 0 to 50 pbw amine having at least 6 nitrogen atoms (N6 and higher amine); or a suitable ratio of 0 to 20 pbw amine having 4 nitrogen atoms (N4), 50 to 95 pbw amine having 5 nitrogen atoms (N5), and 0 to 40 pbw amine having at least 6 nitrogen atoms (N6 and higher amine); or a suitable ratio of 0 to 20 pbw amine having 4 nitrogen atoms (N4), 50 to 90 pbw amine having 5 nitrogen atoms (N5), and 3 to 35 pbw amine having at least 6 nitrogen atoms (N6 and higher amine); or a suitable ratio of 1 to 15 pbw amine having 4 nitrogen atoms (N4), 50 to 90 pbw amine having 5 nitrogen atoms (N5), and 5 to 35 pbw amine having at least 6 nitrogen atoms (N6 and higher amine); or a suitable ratio of 0 to 25 pbw amine having 4 nitrogen atoms (N4), 40 to 95 pbw amine having 5 nitrogen atoms (N5), and 0 to 45 pbw amine having at least 6 nitrogen atoms (N6 and higher amine); or a suitable ratio of 1 to 20 pbw amine having 4 nitrogen atoms (N4), 40 to 90 pbw amine having 5 nitrogen atoms (N5), and 0 to 35 pbw amine having at least 6 nitrogen atoms (N6 and higher amine). "Dimerized" or "dimer" or "polymerized" fatty acid refers, in a general way, to polymerized fatty acids obtained from unsaturated fatty acids. In the present invention, dimer acids and dimer fatty acids are used interchangeably. Common monofunctional unsaturated fatty acids used in making the dimer fatty acid compositions include, but are not limited to, fatty acids occurring in natural oils, such as tall oil, linseed oil, tung oil, perilla oil, oiticica oil, cornseed oil, sunflower oil, safflower oil, dehydrated castor oil, more commonly tall oil fatty acid (TOFA), soya oil fatty acid, and cottonseed oil fatty acid. The dimer fatty acids are prepared by polymerizing the fatty acids under pressure, and then removing most of the unreacted fatty mono-acids by distillation. The final product includes mostly dimeric fatty acids, but includes trimeric as well as some higher fatty acids. The ratio of dimeric fatty acids to trimeric and higher fatty acids is variable, depending on processing conditions and the unsaturated fatty acid feedstock. The dimer fatty acid may also be further processed by, for example, hydrogenation, which reduces the degree of unsaturation and the color of the product.

Suitable for the purposes of the present invention are dimer fatty acids with a dimer content as measured by gas chromatography (GC) ranging from about 50 wt % to about 95 wt %, and a trimer and higher fatty acid (more than two acid group per molecule) content of from about 3 wt % to about 40 wt %, the remainder being monomeric fatty acids. However, as the amount of trimer fatty acid is increased, it is necessary to increase the amount of polyamine and/or the amount of fatty mono-acid in order to maintain the desired viscosity of the final product, since the higher functionality of the trimeric and higher fatty acids leads to more branching and an increase in the molecular weight of the product, and may even gel the product, as will be appreciated by those skilled in the art. Esters of dimer fatty acids, particularly the C1 to C4 alkyl esters, may also be employed in embodiments of the present invention.

Preferred dimer fatty acid components are those with a range of dimeric fatty acids from 75 wt % to 90 wt %. These dimer fatty acids components include Empol® 1018 and Empol® 1019 (Cognis Corp.), Haridimer 250S (Harima M.I.D., Inc.), Yonglin YLD-70 (Jiangsu Yonglin Chemical Oil Co.), and Unidyme® 18 (Arizona Chemical Co.).

The monofunctional fatty acids (also referred to as fatty acids) used in the present invention to prepare amidoamines or in combination with the dimer fatty acids to prepare polyamides include C8 to C22, preferably C16 to C22, mono-carboxylic acids containing from 0 to about 4 units of unsaturation. Usually, such fatty acids are mixtures derived from triglycerides of natural products, such as babassu, castor, coconut, corn, cottonseed, grapeseed, hempseed, kapok, linseed, wild mustard, oiticica, olive, ouri-curi, palm, palm kernel, peanut, perilla, poppyseed, rapeseed, safflower, sesame, soybean, sugarcane, sunflower, tall, teaseed, tung, uchuba, or walnut oils. Saturated and unsaturated pure fatty acids or mixtures of pure fatty acids, such as stearic, palmitic, oleic, linoleic, linolenic, etc., fatty acids may also be employed, as various esters of any of these fatty acids, particularly the C1 to C4 esters. Also of utility is isostearic acid, also known as monomer acid. Monomer acid is the mostly C18 fatty mono-acid stream derived from the preparation of dimer fatty acid. Appropriate synthetic fatty acids can also serve as starting material for amidoamine and polyamide curing agents. The fatty acid can be used individually or as a mixture of more than one fatty acids. Commonly used fatty acids include tall oil fatty acid (TOFA), soya oil, linseed oil, cottonseed oil, or the like. More suitable fatty acids are tall oil fatty acid (TOFA), cottonseed fatty acid, and soya fatty acid.

If desired, other monofunctional and multifunctional carboxylic acids may be incorporated into the reaction composition of amidoamines and polyamides to provide specialized property enhancement. An exemplary property from using lower molecular weight (poly)acid is a reduction of the amine hydrogen equivalent weight (AHEW) which will reduce the amount of the polyamide or of amidoamine used to cure the epoxy.

The amine component used to prepare amidoamines and polyamides includes at least one multifunctional amine of structure (I). In one exemplary embodiment of the present invention, $R_1$ is H in structure (I). In another exemplary embodiment, $R_1$ is $CH_3CH_2CH_2N-$. In yet another embodiment, $R_1$ is a substituted or un-substituted benzyl group of C7-C21. In another embodiment, $R_1$ is a C1-C21 alkyl, or C1-C21 alkenyl group derived from the reaction of monoglycidyl ether of corresponding alcohol or phenol with the secondary amine NH before $R_1$ is attached.

The multifunctional amines of structure (I) of the present invention include, but are not limited to, N-3-aminopropyl diethylenetriamine (N4); N-3-aminopropyl-[N'-3-[N-3-aminopropyl]aminopropyl]diethylenetriamine (N6); N,N'-bis(3-aminopropyl)diethylenetriamine (N5); N,N-bis(3-aminopropyl)diethylenetriamine (N5); N,N,N'-tris(3-aminopropyl)diethylenetriamine (N6); N,N',N''-tris(3-aminopropyl)diethylenetriamine (N6); N,N,N',N'-tetrakis(3-aminopropyl)diethylenetriamine (N7); N,N-bis(3-aminopropyl)-[N'-3-[N-3-aminopropyl]aminopropyl]-[N'-3-aminopropyl]diethylenetriamine (N8); N-3-aminopropyl-[N'-3-[N-3-aminopropyl]aminopropyl]-[N'-3-aminopropyl]diethylenetriamine (N7); These multifunctional amines may be prepared by the Michael reaction of diethylenetriamine with acrylonitrile, followed by hydrogenation over metal catalysts as is well known to those skilled in the art. In one embodiment, the multifunctional amines comprise a mixture of amine represented by structure (I) having 4 nitrogen atoms (N4), having 5 nitrogen atoms (N5), and having at least 6 nitrogen atoms (N6 and higher amine). Each of amine N4, N5, N6 and higher amines in the mixture may contain more than one structural isomers. A representative reaction scheme is shown below.

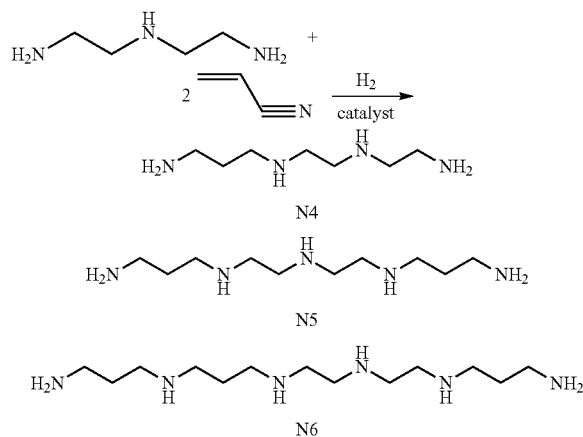

A suitable multifunctional amine represented by structure (I) for use as the amine component to prepare amidoamines and polyamides is N,N'-bis(3-aminopropyl)diethylenetriamine (N5). Suitable multifunctional amines represented by structure (I) include a mixture comprising in a parts-by-weight (pbw) ratio of 0 to 50 pbw amine having 4 nitrogen atoms (N4), 40 to 95 pbw amine having 5 nitrogen atoms (N5), and 0 to 50 pbw amine having at least 6 nitrogen atoms (N6 and higher amine), or a more suitable ratio of 0 to 30 pbw amine having 4 nitrogen atoms (N4), 40 to 95 pbw amine having 5 nitrogen atoms (N5), and 0 to 50 pbw amine having at least 6 nitrogen atoms (N6 and higher amine); or a suitable ratio of 0 to 20 pbw amine having 4 nitrogen atoms (N4), 50 to 95 pbw amine having 5 nitrogen atoms (N5), and 0 to 40 pbw amine having at least 6 nitrogen atoms (N6 and higher amine); or a suitable ratio of 0 to 20 pbw amine having 4 nitrogen atoms (N4), 50 to 90 pbw amine having 5 nitrogen atoms (N5), and 3 to 35 pbw amine having at least 6 nitrogen atoms (N6 and higher amine); or a suitable ratio of 1 to 15 pbw amine having 4 nitrogen atoms (N4), 50 to 90 pbw amine having 5 nitrogen atoms (N5), and 5 to 35 pbw amine having at least 6 nitrogen atoms (N6 and higher amine); or a suitable ratio of 0 to 25 pbw amine having 4 nitrogen atoms (N4), 40 to 95 pbw amine having 5 nitrogen atoms (N5), and 0 to 45 pbw amine having at least 6 nitrogen atoms (N6 and higher amine); or a suitable ratio of 1 to 20 pbw amine having 4 nitrogen atoms (N4), 40 to 90 pbw amine having 5 nitrogen atoms (N5), and 0 to 35 pbw amine having at least 6 nitrogen atoms (N6 and higher amine). Such a mixture can be prepared by the reaction sequence described above for making the multifunctional amine without the need to conduct a distillation or other process of separation, except for the optional removal of low molecular weight side products of the reaction which are more volatile than N-3-aminopropyldiethylenetriamine. It will be recognized by those skilled in the art that small quantities of other products of hydrogenation may be present in the mixture.

In some embodiments, the multifunctional amines include a mixture of multifunctional amines of the present invention. In other embodiments, the curing agent composition is based on a mixture of multifunctional amines of the present invention.

If desired, the curing agent composition may be modified by incorporation of other multifunctional amines having three (3) or more active amine hydrogens. Non-limiting examples of multifunctional amines having three (3) or more active amine hydrogens that are within the scope of the present invention include, but are not limited to, an aliphatic amine, a cycloaliphatic amine, an aromatic amine, a poly(alkylene oxide) diamine or triamine, a Mannich base derivative of an aliphatic amine, a cycloaliphatic amine, or an aromatic amine, a polyamide derivative of an aliphatic amine, a cycloaliphatic amine, or an aromatic amine with a dimer fatty acid or a mixture of a dimer fatty acid and fatty acid, an amidoamine derivative of an aliphatic amine, a cycloaliphatic amine, or an aromatic amine with a fatty acid, an amine adduct derivative of an aliphatic amine, a cycloaliphatic amine, or an aromatic amine with a glycidyl ether of bisphenol A or bisphenol F or an epoxy novolac resin, and the like, or any combination thereof.

Specific examples of multifunctional amines having three (3) or more active amine hydrogens include, but are not limited to, ethylenediamine, diethylenetriamine, triethylenetetramine, tetraethylenepentamine, higher polyethylene amines, aminoethylpiperazine, meta-xylylenediamine, the various isomers of diamine-cyclohexane, isophorone diamine, 3,3'-dimethyl-4,4'-diaminodicyclohexyl methane, 4,4'-diaminodicyclohexyl methane, 2,4'-diaminodicyclohexyl methane, the mixture of methylene bridged poly(cyclohexyl-aromatic)amines (MBPCAA) described in U.S. Pat. No. 5,280,091, 1,2-propylenediamine, 1,3-propylenediamine, 1,4-butanediamine, 1,5-pentanediamine, 1,3-pentanediamine, 1,6-hexanediamine, 3,3,5-trimethyl-1,6-hexane-diamine, 3,5,5-trimethyl-1,6-hexanediamine, 2-methyl-1,5-pentanediamine, bis-(3-amino-propyl)amine, N,N'-bis-(3-aminopropyl)-1,2-ethanediamine, N-(3-aminopropyl)-1,2-ethanediamine, 1,2-diaminocyclohexane, 1,3-diaminocyclohexane, 1,4-diamino-cyclohexane, poly(alkylene oxide)diamines and triamines (such as, for example, JEFFAMINE® D-230, JEFFAMINE® D-400, JEFFAMINE® D-2000, JEFFAMINE® D-4000, JEFFAMINE®

T-403, JEFFAMINE® EDR-148, JEFFAMINE® EDR-192, JEFFAMINE® C-346, JEFFAMINE® ED-600, JEFFAMINE® ED-900, JEFFAMINE® ED-2001) and also aminopropylated ethylene glycols, propanediols, butanediols, hexanediols, polyethylene glycols, polypropylene glycols and polybutanediols. JEFFAMINE® is a federally registered trademark of Huntsman Corporation. The polyamide and amidoamine curative composition may either be modified by incorporating these polyamines in the condensation reaction with the dimer fatty acid and/or monofunctional fatty acids, or by adding them to the polyamide or amidoamine after completion of the condensation reaction. In the former case, it is then necessary to adjust the ratio of moles of polyamine to equivalents of acid to conform with the guidelines given below.

In one exemplary embodiment, the present invention provides a curing agent composition comprising the contact product of:
  (i) a polyamide curing agent comprising the reaction products of (1) an amine component including at least one multifunctional amine of structure (I) with (2) a dimer fatty acid or ester component, optionally, containing a monofunctional fatty acid or ester; and
  (ii) at least one multifunctional amine having three or more active amine hydrogens.

In another exemplary embodiment, the present invention provides a curing agent composition comprising the contact product of:
  (i) an amidoamine curing agent comprising the reaction products of (1) an amine component including at least one multifunctional amine of structure (I) with (2) a monofunctional fatty acid or ester, optionally, containing a dimer fatty acid or ester; and
  (ii) at least one multifunctional amine having three or more active amine hydrogens.

The term "contact product" is used herein to describe compositions wherein the components are contacted together in any order, in any manner, and for any length of time. For example, the components can be contacted by blending or mixing. Further, contacting of any component can occur in the presence or absence of any other component of the compositions or formulations described herein. Still further, two or more of the components of the contact product may react to form other components composing the composition. Combining additional materials or components can be done by any method known to one of skill in the art.

For polyamide synthesis, the percentage of equivalents of fatty mono-acids to total equivalents of monofunctional plus dimer acids and higher-functional fatty acids (more than two acid group per molecule) may be varied within the range of from 0% to about 30%, and a suitable range from 3% to 20%. The equivalents of acid may be obtained by titration of the starting materials with alcoholic hydroxide, as is well known in the art. Those skilled in the art will recognize that increasing the percentage of monofunctional fatty acid lowers the molecular weight and viscosity of the polyamide. They will also recognize that increasing the trimer and higher fatty acid content of the dimer fatty acid increases the molecular weight and viscosity of the polyamide.

For polyamide synthesis, the ratio of total moles of multifunctional amine to equivalents of acid, along with the functionality of the multifunctional amine, are important parameters in determining the molecular weight, viscosity, and other properties of the resulting polyamides. Indeed, if the ratio of amine to acid is not large enough, then the entire composition may gel. Furthermore, this ratio also influences the amine hydrogen equivalent weight (AHEW) of the final product and has an effect upon the amount of unreacted multifunctional amine present after completion of the condensation reaction. Unreacted multifunctional amine can cause deleterious effects to surface appearance and intercoat adhesion. If desired, unreacted multifunctional amine may be removed by vacuum distillation. Suitable ratios of moles of multifunctional amine to equivalents of acid range from about 0.4:1 to about 1.5:1, or from 0.5:1 to 1:1.4, or from 0.6:1 to 1.4:1, or from 0.8:1 to 1.3:1, or from 0.9:1 to 1.3:1. The moles of amine are calculated from the number average molecular weight, if a mixture of amines is employed.

For amidoamine synthesis, optionally dimer fatty acids may be employed in the reaction mixture to enhance certain property, such as flexibility. The percentage of equivalents of dimer fatty acids to total equivalents of monofunctional fatty acids plus dimer acids and higher-functional fatty acids may be varied within the range of from 0% to about 30%, and a suitable range from 2% to 20%, or from 2% to 15%, or from 2% to 10%, or from 2% to 8%. Thus, the percentage of equivalents of monofunctional fatty acids to total equivalents of monofunctional fatty acids plus dimer acids and higher-functional fatty acids may be varied within the range of at least 70%, or at least 80%, or at least 90%. Those skilled in the art will recognize that increasing the percentage of dimer acids and higher-functional fatty acids increases the molecular weight and viscosity of the amidoamine.

Similar to the polyamide synthesis, the ratio of total moles of multifunctional amine to equivalents of acid, along with the functionality of the multifunctional amine, are important parameters in determining the molecular weight, viscosity, and other properties of the resulting amidoamines. Furthermore, this ratio also influences the amine hydrogen equivalent weight (AHEW) of the final product and has an effect upon the amount of unreacted multifunctional amine present after completion of the condensation reaction. Excess amounts of unreacted multifunctional amine after the condensation reaction can be removed by vacuum distillation from the final amidoamines to achieve desired amounts of unreacted multifunctional amine in the amidoamine product. The amount of unreacted free multifunctional amine in the final amidoamine is a range from 0 wt % to 30 wt %, or from 0 wt % to 25 wt %, or from 0 wt % to 20 wt %, or from 3 wt % to 30 wt %, or from 3 wt % to 25 wt %, or from 3 wt % to 20 wt % to the total product composition. Suitable ratios of moles of multifunctional amine to equivalents of acid range from about 0.4:1 to about 2:1, a more suitable range of 0.5:1 to 2:1, or 0.5:1 to 1.8:1, or 0.5:1 to 1.6:1, or 0.6:1 to 1.5:1, or 0.6:1 to 1.4:1, or 0.7:1 to 1.4:1, or 0.8:1 to 1.4:1, or 0.8:1 to 1.5:1.

Polyamides and amidoamines of the present invention may be manufactured by any number of processes known to those skilled in the art. Normally, the amines and acids are combined at temperatures ranging from about room temperature to about 100 degrees Celsius. Heat is then supplied to raise the temperature as water is condensed from the reaction mixture. The reaction temperature ranges from 100 degrees Celsius to 300 degrees Celsius, or from 120 degrees Celsius to 300 degrees Celsius, or from 140 degrees Celsius to 300 degrees Celsius, or from 150 degrees Celsius to 300 degrees Celsius. Heating is normally continued until the specified amount of water is removed that yields a product with the desired amide and imidazoline and/or tetrahydropyrimidine content. Optionally, vacuum may be applied particularly in the late stages of the process to aid in the removal of water from the mixture. To reduce foaming, which can be a problem particularly under vacuum conditions, small amounts of defoamers may be added to the polyamide composition. Appropriate defoamers include various acrylic copolymers containing 2-ethylhexyl acrylate as part of the copolymer composition, various polysiloxane copolymers, and the like.

During the condensation reaction, it is possible to cause some of the amine functional amides to cyclize intramolecular with further loss of water to form tetrahydropyrimidines or imidazolines, as shown below. This results in amidoamines and polyamides containing amine groups to cure the epoxy, amide content, imidazoline and/or tetrahydropyrimidine content.

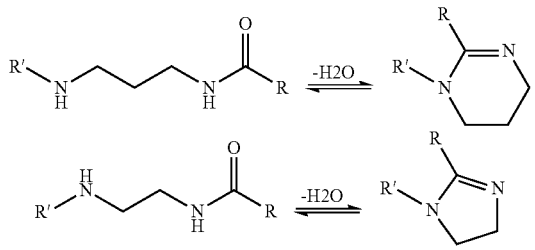

The reaction is continued until substantially all of the carboxylic acid groups are reacted. At that stage, some imidazoline and/or tetrahydropyrimidine has formed especially in the polyamide synthesis, up to 5 mole %. Driving the reaction to form higher levels of tetrahydropyrimidines and/or imidazolines may influence the properties of the polyamide and amidoamine curing agent, such as, for instance, lower viscosity, and improving the appearance of the coating and adhesion to substrate. All possible levels of tetrahydropyrimidine and/or imidazoline functionality of the polyamide curing agents are considered to be part of the present invention. However, in one desirable aspect of the present invention, the polyamide curing agent composition comprises at least 10 mol % tetrahydropyrimidine-containing components, or at least 15 mol %, or at least 20 mol % tetrahydropyrimidine-containing components, as determined by 13C NMR. In some aspects, an upper limit for the tetrahydropyrimidine-containing components would be 75 mol %.

In another desirable aspect of the present invention, the amidoamine curing agent composition comprises at least 2 mol % tetrahydropyrimidine-containing components, or at least 3 mol % tetrahydropyrimidine-containing components, preferably at least 4 mol %, and especially at least 5 mol %, or at least 7 mol %, or at least 10 mol % of tetrahydropyrimidine-containing components, as determined by 13C NMR. In some aspects, an upper limit for the tetrahydropyrimidine-containing components would be 55 mol %, or an upper limit of 65 mol %, or an upper limit of 75 mol %.

The amide functionality of the polyamide and amidoamine curing agents is less than 90 mol % as determined by 13C NMR, or less than 80 mol %, or less than 75 mol %, or less than 70 mol %, or less than 60 mol %, or less than 50 mol %, or less than 40 mol %.

The amidoamine of the present invention has the benefit of remaining liquid at a wide temperature range from above 5 degrees Celsius. Amidoamines prepared from polyethylenes polyamines, such as DETA and TETA, solidify even at ambient temperature, about 25 degrees Celsius.

The polyamide curing agent composition has a viscosity in the range from 50 centipoises to 350,000 centipoises at 25 degrees Celsius, or in the range from 500 centipoises to 150,000 centipoises, or from 1000 to 100,000 centipoises, or from 1500 to 80,000 centipoises, or from 1500 to 50,000 centipoises, or from 1500 to 45,000 centipoises, or from 1500 to 40,000 centipoises at 25 degrees Celsius.

The amidoamine curing agent composition has a viscosity in the range from 50 centipoises to 100,000 centipoises at 25 degrees Celsius, or in the range from 100 centipoises to 80,000 centipoises, or from 100 to 50,000 centipoises, or from 100 to 40,000 centipoises, or from 100 to 30,000 centipoises, or from 100 to 10,000 centipoises, or from 100 to 8,000 centipoises, or from 100 to 5,000 centipoises, or from 100 to 3,000 centipoises, or from 100 to 2,500 centipoises, or from 100 to 2,000 centipoises, or from 100 to 1,800 centipoises, or from 100 to 1,500 centipoises, or from 200 to 1,500 centipoises, or from 200 to 1,000 centipoises, or from 200 to 900 centipoises, or from 200 to 800 centipoises at 25 degrees Celsius.

Generally, the polyamide and amidoamine curing agent composition has an amine hydrogen equivalent weight (AHEW) based on 100% solids from about 30 to about 1,000. Further, the curing agent composition can have an AHEW based on 100% solids from about 50 to about 800, or from about 50 to about 800, or from about 50 to about 700, or from about 50 to about 600, or from about 50 to about 550, or from about 50 to about 500, or from about 50 to about 550, or from about 50 to about 500, from about 50 to about 550, or from about 50 to about 400, or from about 50 to about 350, or from about 50 to about 300, or from about 50 to about 250, or from about 50 to about 200, or from about 50 to about 180, or from about 50 to about 150, or from about 50 to about 125. The polyamide and amidoamine curing agent composition has an amine value based on 100% solids of 100 to 1000 mgKOH/g determined by titration.

It is also possible to modify the polyamides and amidoamine of the present invention by reacting a modest portion of the amine hydrogen with difunctional and/or monofunctional epoxy resins. This is a common practice well known to those skilled in the art, and generally referred to as "adduction". By adducting with difunctional and monofunctional epoxy resins, it is possible to improve the compatibility of the polyamide and amidoamine with epoxy resin and thereby reduce problems, such as blush, carbonation, and exudation and to increase pot life. On the other hand, such modification tends to increase viscosity, particularly in the case of difunctional epoxy resins, and may in some cases also decrease the rate of cure. Particularly useful epoxy resins for adduction include the diglycidyl ethers of bisphenol-A, the advanced diglycidyl ethers of bisphenol-A, the diglycidyl ethers of and bisphenol-F, styrene oxide, cyclohexene oxide, and the glycidyl ethers of phenol, the cresols, tert-butylphenol and other alkyl phenols, butanol, 2-ethylhexanol, and C8 to C14 alcohols and the like. It is also possible to accomplish a modest level of adduction by mixing the amine and epoxy components and allowing them to stand for a period of time known as an induction period to those skilled in the art, normally 15 to 60 minutes, before application.

Additionally, the polyamide and amidoamine curing agent compositions of the present invention can be solvent-based. Alternatively, in another aspect of the present invention, these compositions can further comprise at least one diluent, such as, for example, an organic solvent, or an organic or inorganic acid. Appropriate organic solvents are well known to those skilled in the art of amine formulation chemistry. Exemplary organic solvents suitable for use in the present invention include, but are not limited to, benzyl alcohol, isopropanol, butanol, toluene, xylene, methyl ethyl ketone, Dowanol™ solvents (from Dow Chemicals), and the like, or combinations thereof. Non-limiting examples of organic and inorganic acids are acetic acid, sulfamic acid, lactic acid, adipic acid, salicylic acid, sebacic acid, boric acid, phosphoric acid, p-toluene sulfonic acid, and the like, or combinations thereof. Such acids can increase the curing speed of the curing agent composition.

Curing agent compositions in accordance with the present invention can further comprise at least one multifunctional amine. Multifunctional amine, as used herein, describes compounds with amine functionality and which contain three (3) or more active amine hydrogens.

Non-limiting examples of multifunctional amines having three (3) or more active amine hydrogens that are within the scope of the present invention include, but are not limited to, an aliphatic amine, a cycloaliphatic amine, an aromatic amine, a poly(alkylene oxide) diamine or triamine, a Mannich base derivative of an aliphatic amine, a cycloaliphatic amine, or an aromatic amine, a polyamide derivative of an aliphatic amine, a cycloaliphatic amine, or an aromatic amine with a dimer fatty acid, or a mixture of a dimer fatty acid and fatty acid, an amidoamine derivative of an aliphatic amine, a cycloaliphatic amine, or an aromatic amine with a fatty acid, an amine adduct derivative of an aliphatic amine, a cycloaliphatic amine, or an aromatic amine with a glycidyl ether of bisphenol A or bisphenol F or an epoxy novolac resin, and the like, or any combination thereof.

Embodiments of the present invention include amine-epoxy compositions. The amine-epoxy compositions include a polyamide or an amidoamine curing agent and at least one multifunctional epoxy resin. For example, an amine-epoxy composition, in accordance with the present invention, includes:
  A) an amidoamine curing agent composition comprising the reaction products of (1) an amine component including at least one multifunctional amine of structure (I) with (2) a monofunctional fatty acid or ester component, optionally, containing a dimer fatty acid or ester; and
  B) an epoxy composition comprising at least one multifunctional epoxy resin.

Another embodiment of the present invention includes an amine-epoxy composition comprising:
  A) a polyamide curing agent composition comprising the reaction products of (1) an amine component including at least one multifunctional amine of structure (I) with (2) a dimer fatty acid or ester component, optionally, containing a monofunctional acid or ester; and
  B) an epoxy composition comprising at least one multifunctional epoxy resin.

Optionally, various additives can be present in the compositions or formulations used to produce fabricated articles, dependent upon the desired properties. These additives can include, but are not limited to, solvents (including water), accelerators, plasticizers, fillers, fibers, such as glass or carbon fibers, pigments, pigment dispersing agents, rheology modifiers, thixotropes.

In yet another aspect of the present invention, a method for forming cured epoxy includes reacting a polyamide or an amidoamine curing agent with at least one multifunctional epoxy resin.

Amine-epoxy compositions of the present invention comprise the reaction product of a curing agent composition and an epoxy composition comprising at least one multifunctional epoxy resin. Multifunctional epoxy resin, as used herein, describes compounds containing 2 or more 1,2-epoxy groups per molecule. Epoxide compounds of this type are well known to those of skill in the art and are described in Y. Tanaka, "Synthesis and Characteristics of Epoxides", in C. A. May, ed., *Epoxy Resins Chemistry and Technology* (Marcel Dekker, 1988), which is incorporated herein by reference in its entirety.

One class of epoxy resins suitable for use in the present invention comprises the glycidyl ethers of polyhydric phenols, including the glycidyl ethers of dihydric phenols. Illustrative examples include, but are not limited to, the glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl) propane, 2,2-bis-(4-hydroxyphenyl)-propane (commercially known as bisphenol A), bis-(4-hydroxyphenyl)-methane (commercially known as bisphenol F, and which may contain varying amounts of 2-hydroxyphenyl isomers), and the like, or any combination thereof. Another class of epoxy resins suitable for use in the present invention comprises epoxy novolac resins, which are the glycidyl ethers of novolac resins. Particular suitable epoxy resins are the diglycidyl ethers of bisphenol-A (DGEBA), advanced or higher molecular weight version of DGEBA, diglycidyl ethers of bisphenol-F, epoxy novolac resins, or any combination thereof.

DGEBA or advanced DGEBA resins are often used in coating formulations due to a combination of their low cost and generally high performance properties. Commercial grades of DGEBA having an EEW ranging from about 174 to about 250, and more commonly from about 185 to about 195, are readily available. At these low molecular weights, the epoxy resins are liquids and are often referred to as liquid epoxy resins. It is understood by those skilled in the art that most grades of liquid epoxy resin are slightly polymeric, since pure DGEBA has an EEW of 174. Resins with EEW's between 250 and 450, also generally prepared by the advancement process, are referred to as semi-solid epoxy resins because they are a mixture of solid and liquid at room temperature. The epoxy resins having EEW of from about 450 to 3000 or more are often referred to as solid epoxy resins. Generally, multifunctional epoxy resins with EEW's based on solids of about 160 to about 750 are useful in the present invention. In one aspect of the present invention, the multifunctional epoxy resin has an EEW in a range from about 170 to about 250.

The relative amount chosen for the epoxy composition versus that of the curing agent composition, or hardener, can vary depending upon, for example, the end-use article, its desired properties, and the fabrication method and conditions used to produce the end-use article. For instance, in coating applications using certain amine-epoxy compositions, incorporating more epoxy resin relative to the amount of the curing agent composition can result in coatings which have increased drying time, but with increased hardness and improved appearance as measured by gloss. Amine-epoxy compositions of the present invention generally have stoichiometric ratios of epoxy groups in the epoxy composition to amine hydrogens in the curing agent composition (epoxy to amine stoichiometric ratio) ranging from about 1.5:1 to about 1:1.5, or from about 1.4:1 to about 1:1.4, or from about 1.3:1 to about 1:1.3, or from about 1.2:1 to about 1:1.2.

Depending upon the end-use application, it can be beneficial to reduce the viscosity of the amine-epoxy compositions of the present invention by modifying the epoxy resin composition. For example, the viscosity can be reduced to allow an increase in the level of pigment in a formulation or composition while still permitting easy application, or to allow the use of a higher molecular weight epoxy resin. Thus, it is within the scope of the present invention for the epoxy resin composition, which comprises at least one multifunctional epoxy resin, to further comprise a monofunctional epoxide. Examples of monofunctional epoxides include, but are not limited to, styrene oxide, cyclohexene oxide, ethylene oxide, propylene oxide, butylene oxide, and the glycidyl ethers of phenol, cresols, tert-butylphenol, other alkyl phenols, butanol, 2-ethylhexanol, C4 to C14 alcohols, and the like, or combinations thereof. The multifunctional epoxy resin can also be present in a solution or emulsion, with the medium being water, an organic solvent, or a mixture thereof.

In some circumstances it may be advantageous to incorporate so-called accelerators for the epoxy-amine curing reaction in amine-epoxy composition based on polyamides and amidoamines of the present invention. Such accelerators are well-known to those skilled in the art. Suitable accelerators include, but are not limited to, various organic acids, alcohols, phenols, tertiary amines, hydroxylamines, and the like. Particularly useful accelerators include benzyl alcohol, phenol, alkyl substituted phenols, such as nonylphenol, octylphenol, t-butylphenol, cresol and the like, bisphenol-A, salicylic acid, p-toluene sulfonic acid, dimethylaminomethylphenol, bis(dimethylaminomethyl)phenol, and tris(dimethylaminomethyl)phenol. Normally, such accelerators are used at levels of 15% or less based on the total weight of binder, and more usually at levels of less than 10%, or at levels of less than 5%.

In some circumstances it may be advantageous to incorporate plasticizers for the epoxy-amine network in formulations based on polyamides and amidoamines of the present invention. This is particularly useful in cases where, in the absence of such a plasticizer, the glass transition temperature, $T_g$, of the composition significantly exceeds the ambient temperature before the degree of reaction necessary to meet certain requirements, such as solvent and chemical resistance, and tensile strength has been achieved. Such plasticizers are well known to those skilled in the art. Particularly useful plasticizers include benzyl alcohol, nonylphenol, and various esters of phthalic acid. The ester plasticizers are preferably incorporated in the same package as the epoxy resin to minimize reaction with the amine curing agent. Another particularly useful class of plasticizers are hydrocarbon resins, which include toluene-formaldehyde condensates, such as Epodil® L, xylene-formaldehyde condensates, such as Nikanol® Y50, coumarone-indene resins, and many other hydrocarbon resin modifiers well known to those skilled in the art.

Amine-epoxy compositions of the present invention can be used to produce various articles of manufacture. Depending on the requirements during the manufacturing of or for the end-use application of the article, various additives can be employed in the formulations and compositions to tailor specific properties. These additives are well known to those skilled in the art, and include, but are not limited to, solvents, fillers, pigments, pigment dispersing agents, rheology modifiers, thixotropes, flow and leveling aids, defoamers, etc. Mixtures of solvents are frequently chosen so as to give the best evaporation rate profile for the system while maintaining solubility of the binder components. Suitable solvents include, but are not limited to, aromatics, aliphatics, esters, ketones, ethers, alcohols, glycols, glycol ethers, and the like. Particularly useful in the formulation are some level of ketones, such as acetone, methyl ethyl ketone, methyl isoamyl ketone, methyl propyl ketone, methyl amyl ketone, diacetone alcohol and the like, which can be used to improve pot life with little or no sacrifice in dry speed. If ester solvents are included in the formulation, it is usually necessary to formulate them in the package containing the epoxy resin, so as to minimize their reaction with the amine curing agent. Sometimes the epoxy resins used in the practice of this invention are supplied in solvent cut versions, and likewise, it may be of value to use the polyamides and amidoamines of the present invention, or other curing agents used in combination with these polyamides and amidoamines, as solvent-cut versions.

The present invention also is directed to articles of manufacture comprising an amine-epoxy composition, as described above. Such articles can include, but are not limited to, an adhesive, a coating, a primer, a sealant, a curing compound, a construction product, a flooring product, a composite product, syntactic foams, laminate, potting compounds, grouts, fillers, cementitious grouts, or self-leveling flooring. Additional components or additives can be used together with the compositions of the present invention to produce articles of manufacture. Further, such coatings, primers, sealants, curing compounds or grouts can be applied to metal or concrete substrates.

Coatings based on these amine-epoxy compositions can be solvent-free or can contain diluents, such as water or organic solvents, as needed for the particular application. Coatings can contain various types and levels of pigments for use in paint and primer applications. Amine-epoxy coating compositions comprise a layer having a thickness ranging from 40 to 400 µm (micrometer), preferably 80 to 300 µm, more preferably 100 to 300 µm, for use in a protective coating applied onto metal substrates. In addition, for use in a flooring product or a construction product, coating compositions comprise a layer having a thickness ranging from 50 to 10,000 µm, depending on the type of product and the required end-properties. A coating product that delivers limited mechanical and chemical resistances comprises a layer having a thickness ranging from 50 to 500 µm, preferably 100 to 300 µm; whereas a coating product, such as, for example, a self-leveling floor that delivers high mechanical and chemical resistances, comprises a layer having a thickness ranging from 1,000 to 10,000 µm, preferably 1,500 to 5,000 µm. Coatings of the present invention are suitable for the painting or coating of large metal objects or concrete substrates including ships, bridges, industrial plants and equipment, and floors. Coatings of the present invention may be applied by any number of techniques including spray, brush, roller, paint mitt, and the like. Coatings of this invention may be applied and cured at temperatures ranging from about 0 degrees Celsius to about 50 degrees Celsius, with temperatures of 10 degrees Celsius to 40 degrees Celsius preferred. If desired, these coatings can also be force cured at temperatures up to 150 degrees Celsius or more.

In order to apply very high solids content or 100% solids coatings of the present invention, plural component spray application equipment can be used, in which the amine and epoxy components are mixed in the lines leading to the spray gun, in the spray gun itself, or by mixing the two components together as they leave the spray gun. Using this technique can alleviate limitations with regard to the pot life of the formulation, which typically decreases as both the amine reactivity and the solids content increases. Heated plural component equipment can be employed to reduce the viscosity of the components, thereby improving ease of application.

Construction and flooring applications include compositions comprising the amine-epoxy compositions of the present invention in combination with concrete or other materials commonly used in the construction industry. Applications of compositions of the present invention include, but are not limited to, composition's use as a primer, a deep penetrating primer, a coating, a curing compound, and/or a sealant for new or old concrete, such as referenced in ASTM C309-97, which is incorporated herein by reference. As a primer or a sealant, the amine-epoxy compositions of the present invention can be applied to surfaces to improve adhesive bonding prior to the application of a coating. As it pertains to concrete and cementitious application, a coating is an agent used for application on a surface to create a protective or decorative layer or a coat. Crack injection and crack filling products also can be prepared from the compositions disclosed herein. Amine-epoxy compositions of the present invention can be mixed with cementitious materials, such as concrete mix, to form polymer or modified cements, tile grouts, and the like. Non-limiting examples of composite products or articles comprising amine-epoxy compositions disclosed herein include tennis rackets, skis, bike frames, airplane wings, glass fiber reinforced composites, and other molded products.

In a particular use of the present invention, these curing agent compositions will have applicability in making epoxy filament-wound tanks, infusion composites, such as windmill blades, aerospace adhesives, industrial adhesives, as well as other related applications. A composite is a material made of different substances, and in the case of resin technologies, composites refer to resin impregnated systems where the resin is reinforced by the addition of reinforcing materials, such as fillers and fibers for improving general properties of the resulting product. These materials work together but are not soluble in one another. In the present case, the binder component comprises the epoxy resin and epoxy curing agent(s). There are many types of composite applications, such as prepegs, laminates, filament windings, braiding, pultrusion, wet lay and infusion composites. Resin infusion, or resin transfer, is a process by which resin is introduced to the composite mold, the reinforcement material having already been placed into the mold and closed prior to resin introduction. There are variations on this process, such as those that are vacuum assisted.

The disclosure is further illustrated by the following examples, which are not to be construed as imposing limitations to the scope of this disclosure. Various other aspects, embodiments, modifications, and equivalents thereof which, after reading the description herein, may suggest themselves to one of ordinary skill in the art without departing from the spirit of the present invention or the scope of the appended claims.

EXAMPLES

Synthesis Examples

Viscosity was measured by a Brookefield viscometer, amine value was determined by a Metrohm titrator, and chemical composition of the amidoamine and polyamides was analyzed by nuclear magnetic resonance (NMR). The NMR experiments were performed at ambient temperature employing the Bruker DRX-400 FT-NMR spectrometer equipped with a 10 mm BBO probe. Quantitative $^{13}$C NMR data was acquired using inverse-gated decoupling, a 45° pulse, and a 6 second relaxation delay. The samples were dissolved in chloroform-d with chromium acetylacetonate added as a relaxation agent. The chemical shift scale was referenced to the solvent peak. The composition of the multifunctional amine represented by Structure (I) was analyzed by gas chromatograph (GC). The amount of unreacted multifunction amine of Structure (I) in amidoamines and polyamides was analyzed by GC as well.

Example 1. Synthesis of Multifunctional Amine Represented by Structure (I)

Step 1. Cyanoethylation of Diethylenetriamine

A 2-gallon Parr reactor was charged with 2,491 g diethylenetriamine (24.2 moles) then sealed. The agitator was started, and the reactor was purged with nitrogen then heated to 70 degrees Celsius. When the temperature was at 70 degrees Celsius, 2,689 g acrylonitrile (50.7 moles) was charged from an Isco pump over 2 hours. The reaction mixture was stirred for 30 minutes at 70 degrees Celsius after the addition was completed. The product then was cooled to ambient temperature and discharged from the reactor into a bottle. Analysis of a sample by GC showed that the mixture contained 0.9% acrylonitrile, 7.8% monocyanoethylated diethylenetriamine, 65.8% dicyanoethylated diethylenetriamine (mixture of isomers), and 23.8% tricyanoethylated diethylenetriamine (mixture of isomers).

Step 2: Semi-Batch Hydrogenation of Cyanoethylated Diethylenetriamine of Step 1

A 2-gallon Parr reactor was charged with 950 g isopropanol, 52 g Raney® cobalt 2724 catalyst, and 87 g 15 wt % aqueous LiOH H$_2$O solution. The reactor was sealed then purged three times with nitrogen, pressure checked, purged three times with hydrogen then pressurized with hydrogen to 600 psig and heated to 145 degrees Celsius. The agitator speed was set to 1000 rpm. When the reaction mixture was at temperature, the hydrogen pressure was increased to 800 psig. Cyanoethylated diethylenetriamine from step 1 above, 2,553 g, was charged to the reactor over 2 hours from an Isco pump. After the charge was completed, the reaction mixture was held at temperature and pressure for 10 minutes. The reactor was cooled, vented, purged with nitrogen, and the contents were discharged through a filter. Water, isopropanol solvent, and low molecular weight components were removed under vacuum using a rotary evaporator. The final product contained 6.2% monoaminopropylated diethylenetriamine (N4), 60.4% diaminopropylated diethylenetriamine (N5) (mixture of isomers), and 24.4% triaminopropylated diethylenetriamine (N6) (mixture of isomers) based on GC analysis.

Example 2. Synthesis of Amidoamine from Example 1

A one-liter glass reactor was equipped with an overhead stirrer, a nitrogen inlet, a distillation head with a 50 mL of graduated receiver. To the glass reactor was added 220.1 g of TOFA (Sylfat FA-1, Arizona Chemical Co.) while purging the system slowly with nitrogen. The stirrer was started after the addition of TOFA. To the reactor was then added 175.5 g of the multifunctional amine of structure (I) from Example 1 over ten minutes and the stirrer rate was increased to 350 rpm. The contents were then heated to 265 degrees Celsius and 17.5 g of distillate was removed by distillation. During the first phase of the reaction, distillate was removed by atmosphere distillation, and vacuum was applied during the second phase of the reaction. After the desired amount of distillate was collected, the reactor was cooled to 65 degrees Celsius and the content was discharged. The final product had an amine value of 438 mg KOH/g, a viscosity of 491 centipoises, and a calculated amine hydrogen equivalent weight (AHEW) of 98. GC analysis showed 13.4% unreacted multifunctional amine of Structure (I). $^{13}$C NMR analysis indicated the product contained 79 mol % of amide, 10 mol % of imidazoline, and 11% of tetrahydropyrimidine.

Example 3. Synthesis of Amidoamine from Example 1

Example 3 utilized the same procedure as Example 2. TOFA 250.0 g was reacted with 199.2 g of the multifunctional amine of Example 1. 28.8 g of distillate was collected. The final product had an amine value of 455 mg KOH/g, a viscosity of 587 centipoises, and a calculated amine hydrogen equivalent weight (AHEW) of 102. GC analysis showed 11.4% unreacted multifunctional amine of Structure (I). $^{13}$C NMR analysis indicated NMR analysis showed the product contained 47 mol % of amide, 16 mol % of imidazoline, and 37% of tetrahydropyrimidine.

Example 4. Synthesis of Amidoamine from Example 1

Example 4 utilized the same procedure as Example 2. TOFA 300.0 g was reacted with 227.5 g of the multifunctional amine of Example 1. 28.5 g of distillate was collected. The final product had an amine value of 426 mg KOH/g, a viscosity of 473 centipoises, and a calculated amine hydrogen equivalent weight (AHEW) of 105. GC analysis showed 17.9% unreacted multifunctional amine of Structure (I). $^{13}$C NMR analysis indicated NMR analysis showed the product contained 67 mol % of amide, 14 mol % of imidazoline, and 19% of tetrahydropyrimidine.

Example 5. Synthesis of Polyamide from Example 1

Example 5 utilized the same procedure as Example 2 except both TOFA and dimer acid reacted with multifunction amine of structure (I). Dimer acid 210.0 g (Yonglin YLD-70), and TOFA 21.8 g were reacted with 180.0 g of the multifunctional amine of Example 1. 22.7 g of distillate was collected. The final product had an amine value of 453 mg KOH/g, a viscosity of 24230 centipoises, and a calculated amine hydrogen equivalent weight (AHEW) of 110. $^{13}$C NMR analysis indicated NMR analysis showed the product contained 67 mol % of amide, 8 mol % of imidazoline, and 25% of tetrahydropyrimidine.

Example 6. Synthesis of Polyamide from Example 1

Example 6 utilized the same procedure as Example 5. Dimer acid 163.1 g (Yonglin YLD-70), and TOFA 104.2 g were reacted with 200.0 g of the multifunctional amine of Example 1. 31.8 g of distillate was collected. The final product had an amine value of 421 mg KOH/g, a viscosity of 6700 centipoises, and a calculated amine hydrogen equivalent weight (AHEW) of 116. $^{13}$C NMR analysis indicated NMR analysis showed the product contained 61 mol % of amide, 14 mol % of imidazoline, and 26% of tetrahydropyrimidine.

Example 7. Synthesis of Amidoamine from Example 1

Example 7 utilized the same procedure as Example 2. TOFA 550.4 g was reacted with 292.1 g of the multifunctional amine of Example 1. 62.7 g of distillate was collected. The final product had an amine value of 313 mg KOH/g, a viscosity of 644 centipoises, and a calculated amine hydrogen equivalent weight (AHEW) of 190. GC analysis showed 7.5% unreacted multifunctional amine of Structure (I). $^{13}$C NMR analysis indicated NMR analysis showed the product contained 35 mol % of amide, 12 mol % of imidazoline, and 53% of tetrahydropyrimidine.

Example 8. Synthesis of Amidoamine from Example 1

Example 8 utilized the same procedure as Example 2. TOFA 500.0 g was reacted with 418.81 g of the multifunctional amine of Example 1. 51.6 g of distillate was collected. The final product had an amine value of 483 mg KOH/g, a viscosity of 344 centipoises, and a calculated amine hydrogen equivalent weight (AHEW) of 97. GC analysis showed 16% unreacted multifunctional amine of Structure (I). $^{13}$C NMR analysis indicated NMR analysis showed the product contained 59 mol % of amide, 13 mol % of imidazoline, and 28% of tetrahydropyrimidine.

Example 9. Synthesis of Amidoamine from Example 1

Example 9 utilized the same procedure as Example 2. TOFA 471.7 g was reacted with 354.3 g of the multifunctional amine of Example 1. 45.3 g of distillate was collected. The final product had an amine value of 441 mg KOH/g, a viscosity of 317 centipoises, and a calculated amine hydrogen equivalent weight (AHEW) of 108. GC analysis showed 14% unreacted multifunctional amine of Structure (I). $^{13}$C NMR analysis indicated NMR analysis showed the product contained 53 mol % of amide, 9 mol % of imidazoline, and 38% of tetrahydropyrimidine.

Comparative Example 1: Synthesis of Amidoamine from TOFA and Aminopropylated Ethylenediamine Aminopropylated ethylenediamine was synthesized according to Example 3 of U.S. Pat. No. 8,293,863. It contains a mixture of N-3-aminopropyl ethylenediamine, N,N'-bis(3-aminopropyl)ethylenediamine, N,N,N'-tris(3-aminopropyl)ethylenediamine, and N,N,N',N'-tetrakis(3-aminopropyl)ethylenediamine.

The amidoamine from aminopropylated ethylenediamine above and TOFA was synthesized using the same procedure as Example 1. TOFA 260.0 g was reacted with 158.8 g of aminopropylated ethylenediamine above. 15.7 g of distillate was collected. The final product had an amine value of 378 mg KOH/g, and a calculated amine hydrogen equivalent weight (AHEW) of 117. $^{13}$C NMR analysis indicated NMR analysis showed the product contained 66 mol % of amide, 5 mol % of imidazoline, and 29% of tetrahydropyrimidine. The product solidified at ambient temperature and thus viscosity was not determined.

Comparative Example 2: Synthesis of Amidoamine from TOFA and Diethylenetriamine The amidoamine from diethylenetriamine and TOFA was synthesized using the same procedure as Example 1 except reaction was carried out at 195 degrees Celsius due to lower boiling point of DETA at 205 degrees Celsius. TOFA 225.4 g was reacted with 129.9 g of DETA. 11.8 g of distillate was collected. The final product had an amine value of 487 mg KOH/g, and a calculated amine hydrogen equivalent weight (AHEW) of 171. The product solidified at ambient temperature and thus viscosity was not determined.

Comparative Example 3: Synthesis of Amidoamine from TOFA and Triethylenetetramine (TETA)

The amidoamine from TETA and TOFA was synthesized using the same procedure as Example 1. TOFA 309.9 g was reacted with 190.1 g of TETA. 20.0 g of distillate was collected. The final product had a calculated amine hydrogen equivalent weight (AHEW) of 111. The product solidified at ambient temperature and thus viscosity was not determined.

Comparative Example 4: Synthesis of Amidoamine from TOFA and Aminopropylation Product of Aminopropylated Ethylenediamine Aminopropylated ethylenediamine was synthesized according to Example 3 of U.S. Pat. No. 8,293,863. It contains a mixture of N-3-aminopropyl ethylenediamine, N,N'-bis(3-aminopropyl)ethylenediamine, N,N,N'-tris(3-aminopropyl)ethylenediamine, and N,N,N',N'-tetrakis(3-aminopropyl)ethylenediamine. The product was aminopropylated again using the same procedure with charge amount for 1). cyanoethylation step: 704.8 g of aminopropylated ethylenediamine, 17.6 g of water and 435 g of acrylonitrile; and 2) hydrogenation step: 1000 g of cyanoethylated aminopropylated ethylenediamine, 15 g of Raney Co catalyst and 200 g of isopropanol. The product is a mixture of amines containing majority component of amine with 6 nitrogen atoms, and minor amine components with 5, 7 and 8 nitrogen atoms.

The above amine product was used to prepare amidoamine with TOFA using the same procedure as Example 1. 320.0 g of TOFA was reacted with 312.5 g of the amine and 26.3 g of distillated was collected. The final product had a calculated amine hydrogen equivalent weight (AHEW) of 122. Some solid formed after 30 days at room temperature. The product was put in oven at 60 degrees Celsius for 1 hour to melt the solid. After 3 days the solid formed again.

Testing of Curing Agents

Curing agent mixtures were prepared by combining and mixing the components given in examples. They were then thoroughly mixed stoichiometrically and thoroughly (amine/epoxy ratio was 1:1) with the epoxy component of standard bisphenol-A based epoxy resin of EPON® 828, EEW 190, unless specified otherwise. ANCAMIDE® 350A (A350A), ANCAMIDE® 375A (A375A), ANCAMIDE® 502 (A502), ANCAMIDE® 503 (A503), and ANCAMIDE® 506 (A506) were obtained from Air Products and Chemicals, Inc. EPON® is a registered trademark of Hexion, Inc. ANCAMINE® is a registered trademark of Air Products And Chemicals, Inc. The test methods are summarized in Table 1. ANCAMIDE® 502, 503 and 506 are conventional amidoamine curing agents based on TEPA and TOFA, with viscosity of 306, 309, and 239, respectively, and recommended phr use level of 50, 50, and 55-60, respectively. ANCAMIDE® 350A and 375A are polyamide curing agents based on dimer acid, TOFA and TETA, with viscosity of 11,000 and 2450 centipoises, and recommended phr use level of 55 and 50, respectively. Examples 5 and 6 are in comparison with ANCAMIDE® 350A and 375A, respectively.

TABLE 1

Test Methods

| Property | Measurements | ASTM METHOD |
| --- | --- | --- |
| Gel time | 150 grams sample | D2471 |
| Drying time | BK recorder Thin film set times Phase 1: set to touch Phase 2: tack free Phase 3: dry hard Phase 4: dry through | D5895 |
| Hardness | Persoz Pendulum Hardness (s) | D4366 |
| | Shore D | D2240 |
| Adhesion | Adhesion to concrete | ASTM D7234 |
| Mechanical property | Tensile strength | D638 Type I |
| | Flexural Strength | ASTM D790 (2" span) |
| | Compressive strength | ASTM D695 |

The gel time characterizes the time a composition transitions from a liquid to a gel. The gel time of the amine-epoxy compositions was measured with a TECHNE gelation timer model FGT 6 using ASTM D2471. One end of the metal rod was connected to the TECHNE gelation timer and the other end with the 22 mm diameter stainless steel plunger. A total of 150 grams of the mixture comprising the liquid amine curing agent composition was mixed stoichiometrically and with the epoxy resin EPON® 828 for 2-3 minutes in an 8 oz. plastic jar at 25 degrees Celsius. The gelation timer was turned to "start/hold" when the mixing started to start the timer. After mixing, the stainless steel plunger was immersed into epoxy-liquid curing agent mixture and gel timer was turned to "start/operate". Gel time was recorded in minutes at 25 degrees Celsius.

The dry time or thin film set time (TFST) was determined using a Beck-Koller recorder, in accordance with ASTM D5895. The amine-epoxy coatings were prepared on standard glass panels at a wet film thickness of about 150 micron WFT (wet film thickness) using a Bird applicator. The coatings were cured at 23 degrees Celsius and 50% relative humidity (RH).

The shore D hardness test results were obtained and 7 days, cure respectively at 23 degrees Celsius and 50% RH. The test coatings were applied to glass panels at 150 micron WFT (wet film thickness) using a Bird type applicator and tested in accordance with ASTM D4366.

Degree of cure and Tg were determined by Dynamic Scanning calorimetry (DSC). About 5 grams of the amine-epoxy composition were mixed for 3 cycles using FlackTeK DAC 250 SP SpeedMixer™ by Hauschild. Around 5-10 mg samples were placed in Tzero hermetic DSC pans and were sealed in air. The samples were cured at 23 degrees Celsius for 7 days, and analyzed using a TA Instruments Q2000 DSC calibrated in T4P mode at a heating rate of 10 degrees Celsius/minute with Indium. The samples were heated from −20 to 280 degrees Celsius at 10 degrees Celsius/minute. The samples were then cooled back to −20 degrees Celsius and the test was repeated. The degree of cure was determined by subtracting the residual heat of cure after 7 days from the initial total heat of cure, then divided by the initial total heat of cure.

Test Example 1. Cold Temperature Storage Stability

Examples 2, 3, and 4 were placed in a refrigerator at 5 degrees Celsius. The samples were stable without visible solid formation for 3 months. In contrast, amidoamine of Comparative examples 1, 2, 3 and 4 solidified at ambient temperature about 25 degrees Celsius.

Test Example 2

Various tests were performed according to methods outlined in Table 1, and data are summarized in Table 2, in comparison with conventional amidoamine ANCAMIDE® 502, 503 and 506. The data showed that the amidoamine of the current invention had very similar property to the conventional amidoamine based on TEPA and TOFA.

Test Example 3. Dry Time of Example 5 and 6 Polyamide

Example 5 was compared with Ancamide 350A, and Example 6 was compared with Ancamide 375A, a conventional polyamide with lower viscosity. The data is summarized in Table 3.

All above-mentioned references are hereby incorporated by reference herein.

While the invention has been described with reference to certain aspects or embodiments, it will be understood by those skilled in the art that various changes may be made and equivalents may be substituted for elements thereof without departing from the scope of the invention. In addition, many modifications may be made to adapt the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

TABLE 2

Test Results Of Amidoamines

| Property | Units | Ancamide 502 | Ancamide 503 | Ancamide 506 | Example 7 | Example 8 | Example 9 |
|---|---|---|---|---|---|---|---|
| Amine Value | mg KOH/g | 455 | 500 | 406 | 313 | 483 | 441 |
| Viscosity | cps | 309 | 306 | 239 | 644 | 344 | 317 |
| Use Level phr | PHR | 50 | 50 | 60 | 60 | 50 | 50 |
| Gel Time | Minutes | 109 | 83 | 294 | 304 | 80 | 96 |
| Shore D −7 day | | 84 | 83 | 85 | 85 | 87 | 86 |
| Thin Film Set Time (6 mil WFT)/25 C. | h | 13.5 | 7.5 | 22.5 | 23.5 | 8.1 | 10.6 |
| Tg DSC, $1^{st}$ scan (7 day) | C. | 62 | 66 | 63 | 58 | 67 | 65 |
| degree of cure | % | 86% | 89% | 93% | 95% | 87% | 88% |
| Pull-Adhesion to Concrete | psi | 906 | 786 | 1081 | 995 | 818 | 1168 |
| failure mode | psi | concrete type A | concrete type A | concrete type A | concrete type A | concrete type A | concrete type A |
| Compressive Strength | MPa | 76 | 78 | 69 | 78 | 83 | 76 |
| Compressive Modulus | GPa | 2.2 | 1.9 | 2 | 2.1 | 2.2 | 2.1 |
| Tensile Strength | MPa | 44 | 44 | 45 | 50 | 48 | 47 |
| Tensile Modulus | GPa | 2.1 | 2.6 | 1.7 | 2.2 | 2.8 | 2.1 |
| Tensile Elongation | % | 6.5% | 5.1% | 5.9% | 6.3% | 6.5% | 6.7% |
| Flexural Strength | MPa | 71 | 96 | 77 | 83 | 100 | 77 |
| Flexural Modulus | GPa | 1.5 | 2.6 | 2.2 | 2.3 | 2.7 | 1.5 |

TABLE 3

Dry Time Of Polyamides

| Curing agents | A350A | Example 5 | A375A | Example 6 |
|---|---|---|---|---|
| Phase 1 (hrs) | 5.8 | 2.5 | 6.8 | 1.8 |
| Phase 2 (hrs) | 8.8 | 3.5 | 11.8 | 7.5 |
| Phase 3 (hrs) | 14.5 | 9.5 | >24 | 16 |
| Coating appearance | clear | Slightly hazy | cloudy | clear |

The invention claimed is:

1. An epoxy curing agent composition consisting of a reaction product of (1) an amine component comprising at least one multifunctional amine of structure (I):

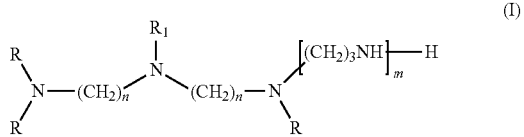

(I)

wherein each R is independently H or CH₂CH₂CH₂NH₂; R₁ is H, CH₂CH₂CH₂NH₂, C1-C21 alkyl, or C1-C21 alkenyl; n is 2; and m is 1 or 2, (2) a fatty acid or ester component consisting of at least one monofunctional fatty acid or ester, and combinations thereof, (3) optionally at least one additional multifunctional amine having three or more active amine hydrogens, (4) optionally at least one accelerator, and (5) optionally at least one diluent; wherein the composition is a liquid at ambient temperature.

2. The composition of claim 1, wherein the monofunctional fatty acid is a C16-C22 monocarboxylic acid having from 0 to 4 units of unsaturation.

3. The composition of claim 1, wherein the monofunctional fatty acid is selected from the group consisting of tall oil fatty acid, linseed oil fatty acid, tung oil fatty acid, perilla oil fatty acid, oiticica oil fatty acid, cornseed oil fatty acid, sunflower oil fatty acid, safflower oil fatty acid, dehydrated castor oil fatty acid, and combinations thereof.

4. The composition of claim 1, wherein the reaction product comprises at least 3 mol % tetrahydropyrimidine-containing components out of 100 mol % reaction product.

5. The composition of claim 1, wherein the reaction product comprises at least 15 mol % tetrahydropyrimidine-containing components out of 100 mol % reaction product.

6. The composition of claim 1, wherein the amine component comprises a compound selected from the group consisting of N-3-aminopropyl diethylenetriamine; N-3-aminopropyl-[N'-3-[N-3-aminopropyl]aminopropyl]diethylenetriamine; N,N'-bis(3-aminopropyl)diethylenetriamine; N,N-bis(3-aminopropyl)diethylenetriamine; N,N,N'-tris(3-aminopropyl)diethylenetriamine; N,N',N''-tris(3-aminopropyl)diethylenetriamine; N,N,N',N'-tetrakis(3-aminopropyl)diethylenetriamine; N, N-bis(3-aminopropyl)-[N'-3-[N-3-aminopropyl]aminopropyl]-[N'-3-aminopropyl] diethylenetriamine; N-3-aminopropyl-[N'-3-[N-3-aminopropyl]aminopropyl]-[N'-3-aminopropyl] diethylenetriamine; and combinations thereof.

7. The composition of claim 1, wherein the amine component comprises a compound wherein R₁ is H or CH₂CH₂CH₂NH₂.

8. The composition of claim 1, wherein the amine component comprises a mixture of amines of structure according to formula (I) in a parts-by-weight (pbw) ratio of 0 to 50 pbw amine having 4 nitrogen atoms, 40 to 95 pbw amine having 5 nitrogen atoms, 0 to 50 pbw amine having at least 6 nitrogen atoms.

9. The composition of claim 1, wherein the amine component comprises a mixture of amines of structure according to formula (I) in a parts-by-weight (pbw) ratio of 0 to 20 pbw amine having 4 nitrogen atoms, 50 to 90 pbw amine having 5 nitrogen atoms, 3 to 35 pbw amine having at least 6 nitrogen atoms.

10. The composition of claim 1, wherein the amine component and the fatty acid or ester component are reacted in a ratio of moles of multifunctional amine to equivalents of acid from about 0.4:1 to about 2.0:1.

11. The composition of claim 1, wherein the at least one accelerator is selected from the group consisting of benzyl alcohol, phenol, nonylphenol, octylphenol, t-butylphenol, cresol, bisphenol-A, salicylic acid, dimethylaminomethylphenol, bis(dimethylaminomethyl)phenol, and tris(dimethylaminomethyl)phenol.

12. The composition of claim 1, wherein the at least one multifunctional amine having three or more active amine hydrogens is selected from the group consisting of an aliphatic amine, a cycloaliphatic amine, an aromatic amine, a poly(alkylene oxide) diamine or triamine, a Mannich base derivative of an aliphatic amine, a cycloaliphatic amine, or an aromatic amine, a polyamide derivative of an aliphatic amine, a cycloaliphatic amine, or an aromatic amine with a dimer fatty acid or a mixture of a dimer fatty acid and fatty acid, an amidoamine derivative of an aliphatic amine, a cycloaliphatic amine, or an aromatic amine with a fatty acid, an amine adduct derivative of an aliphatic amine, a cycloaliphatic amine, or an aromatic amine with a glycidyl ether of bisphenol A or bisphenol F or an epoxy novolac resin, and the like, and combinations thereof.

13. The composition of claim 12, wherein the at least one multifunctional amine is selected from the group consisting of ethylenediamine, diethylenetriamine, triethylenetetramine, tetraethylenepentamine, aminoethylpiperazine, meta-xylylenediamine, the various isomers of diamine-cyclohexane, isophorone diamine, 3,3'-dimethyl-4,4'-diaminodicyclohexyl methane, 4,4'-diaminodicyclohexyl methane, 2,4'-diaminodicyclohexyl methane, the mixture of methylene bridged poly(cyclohexyl-aromatic)amines, 1,2-propylenediamine, 1,3-propylenediamine, 1,4-butanediamine, 1,5-pentanediamine, 1,3-pentanediamine, 1,6-hexanediamine, 3,3,5-trimethyl-1,6-hexane-diamine, 3,5,5-trimethyl-1,6-hexanediamine, 2-methyl-1,5-pentanediamine, bis-(3-amino-propyl)amine, N,N'-bis-(3-aminopropyl)-1,2-ethanediamine, N-(3-aminopropyl)-1,2-ethanediamine, 1,2-diaminocyclohexane, 1,3-diaminocyclohexane, 1,4-diamino-cyclohexane, the poly(alkylene oxide)diamines and triamines, aminopropylated ethylene glycols, aminopropylated propanediols, aminopropylated butanediols, aminopropylated hexanediols, aminopropylated polyethylene glycols, aminopropylated polypropylene glycols, aminopropylated polybutanediols, and combinations thereof.

14. The composition of claim 1, wherein the at least one accelerator is selected from the group consisting of organic acids, alcohols, phenols, tertiary amines, and hydroxylamines.

15. An epoxy system comprising the composition of claim 1 and an epoxy resin.

16. The composition of claim 1, wherein the at least one diluent is selected from the group consisting of benzyl alcohol, isopropanol, butanol, toluene, xylene, methyl ethyl ketone, acetic acid, sulfamic acid, lactic acid, adipic acid, salicylic acid, sebacic acid, boric acid, phosphoric acid, p-toluene sulfonic acid, and combinations thereof.

* * * * *